US005625098A

United States Patent [19]
Kao et al.

[11] Patent Number: 5,625,098
[45] Date of Patent: *Apr. 29, 1997

[54] PROCESS FOR PREPARING N-ALKYL POLYHYDROXYALKYL AMINES IN AQUEOUS/HYDROXY SOLVENTS

[75] Inventors: Junan Kao; Jeffrey J. Scheibel; Robert E. Shumate; Cynthia M. Stark; Roland G. Severson, Jr., all of Cincinnati; Kevin L. Garber, Maineville; Scott A. VanDiest, Cincinnati, all of Ohio

[73] Assignee: The Procter & Gamble Company, Cincinnati, Ohio

[*] Notice: The term of this patent shall not extend beyond the expiration date of Pat. No. 5,449,770.

[21] Appl. No.: 462,343

[22] Filed: Jun. 5, 1995

Related U.S. Application Data

[63] Continuation of Ser. No. 907,382, Jul. 8, 1992, abandoned, which is a continuation-in-part of Ser. No. 736,172, Jul. 26, 1991, abandoned, and Ser. No. 820,712, Jan. 14, 1992, Pat. No. 5,449,770.

[51] Int. Cl.$^6$ .................................................. C07C 209/44
[52] U.S. Cl. .............................................. 564/487; 564/480
[58] Field of Search ........................................ 564/480, 487

[56] References Cited

U.S. PATENT DOCUMENTS

| | | | |
|---|---|---|---|
| 1,985,424 | 12/1934 | Piggott | 260/124 |
| 2,016,962 | 10/1935 | Flint et al. | 260/127 |
| 2,653,932 | 9/1953 | Schwartz | 260/211 |
| 2,662,073 | 12/1953 | Mehltretter et al. | 260/102 |
| 2,703,798 | 3/1955 | Schwartz | 260/211 |
| 2,844,609 | 7/1958 | Tesoro | 260/404 |
| 2,891,052 | 6/1959 | Boettner et al. | 260/211 |
| 2,954,347 | 9/1960 | St. John et al. | 252/109 |
| 2,991,296 | 7/1961 | Scherr | 260/404 |
| 2,993,887 | 7/1961 | Zech | 260/211 |
| 3,257,436 | 6/1966 | Lindner | 260/404 |
| 3,285,856 | 11/1966 | Lew | 252/152 |
| 3,576,749 | 4/1971 | Megson et al. | 252/132 |
| 3,637,495 | 1/1972 | Eckert et al. | 252/8.8 |
| 3,704,228 | 11/1972 | Eckert | 252/117 |
| 3,920,586 | 11/1975 | Bonaparte et al. | 252/531 |
| 3,929,678 | 12/1975 | Laughlin et al. | 252/526 |
| 3,985,669 | 10/1976 | Krummel et al. | 252/116 |
| 3,988,255 | 10/1976 | Seiden | 252/107 |
| 4,094,808 | 6/1978 | Stewart et al. | 252/186 |
| 4,129,511 | 12/1978 | Ogoshi et al. | 252/140 |
| 4,223,163 | 9/1980 | Guilloty | 568/618 |
| 4,292,212 | 9/1981 | Melby | 252/547 |
| 4,483,781 | 11/1984 | Hartman | 252/174.12 |
| 4,540,821 | 9/1985 | Larkin et al. | 564/473 |
| 4,565,647 | 1/1986 | Llenado | 252/354 |
| 4,664,839 | 5/1987 | Rieck | 252/175 |
| 4,704,224 | 11/1987 | Saud | 252/132 |
| 4,843,154 | 6/1989 | Klein et al. | 536/4.1 |
| 5,009,814 | 4/1991 | Kelkenberg et al. | 252/528 |

FOREIGN PATENT DOCUMENTS

| | | |
|---|---|---|
| 206283 | 6/1956 | Australia . |
| 0220676A1 | 5/1987 | European Pat. Off. ...... C07C 103/38 |
| 0255033A2 | 2/1988 | European Pat. Off. .......... C07H 1/04 |
| 0282816A2 | 9/1988 | European Pat. Off. .......... A61K 7/48 |
| 0285768A1 | 10/1988 | European Pat. Off. .......... C11D 3/32 |
| 0422508A2 | 4/1991 | European Pat. Off. ......... A61K 7/06 |
| 1580491 | 9/1969 | France . |
| 2657611 | 8/1991 | France ............................. C07H 5/06 |
| 53839 | 2/1967 | German Dem. Rep. ......... C11D 3/00 |
| 13746 | 9/1957 | Germany . |
| 23346 | 6/1962 | Germany . |
| 2038103 | 2/1972 | Germany ......................... C11D 7/42 |
| 2226872 | 12/1973 | Germany . |
| 2404070 | 8/1975 | Germany . |
| 420518 | 11/1934 | United Kingdom . |
| 519381 | 3/1940 | United Kingdom . |
| 771423 | 4/1957 | United Kingdom . |
| 809060 | 2/1959 | United Kingdom . |
| 2242686 | 10/1991 | United Kingdom ............ C11D 1/722 |

OTHER PUBLICATIONS

The Reaction of Glucose with Some Amines, Mitts and Hixon, JACS, vol. 66, (1944), PP. 483–486.
[23] 1–Amino–1–deoxy–D–glucitol, Long and Bollenback, Meth. Carbohyd. Chem., vol. 2, (1963), pp. 79–83.
Synthesis of $^{14}$C–Labeled N–Methylglucamine, Heeg et al., Can. J. of Pharmaceutical Sciences, vol. 10, No. 3, (1975), pp. 75–76.
Relative Stabilities of d–Glucose–Amine Derivatives, Mohammad and Olcott, JACS, Apr. 1947, p. 969.
Detergents Based on Sugars, Kelkenberg, Tenside Surfactants Detergents, vol. 25, #1 (1988).
Synthesis of Long Chain N–Alkyllactylamines from Unprotected Lactose—A New Series of Non–Ionic Surfactants, Latge et al., J. Dispersion Science and Technology, 12(3&4), pp. 227–237 (1991).
"N–D–Gluco–N–methylalkanamide Compounds, a New Class of Non–Ionic Detergents for Membrane Biochemistry", Biochem. J. (1982), vol. 207, pp. 363–366, Hildreth carbohydrate amphiphiles, Liquid Crystals, 1988, vol. 3, No. 11, pp. 1569–1581, J. W. Goodby et al.

*Primary Examiner*—Brian M. Burn
*Attorney, Agent, or Firm*—Robert B. Aylor

[57] ABSTRACT

Amines such as methyl amine are reacted with materials such as reducing sugars in aqueous/hydroxy solvents such as water and/or methanol to prepare N–alkyl polyhydroxy amines. Accordingly, glucose is reacted with methyl amine and the resulting adduct is hydrogenated to yield N–methylglucamine. The N–alkyl polyhydroxyamines can be subsequently reacted with fatty esters to provide polyhydroxy fatty acid amides useful as detersive surfactants. Thus, detersive surfactants are available from non-petrochemical precursors such as sugars and sugar sources such as corn syrup, and fatty acid esters derivable from various fats and oils.

37 Claims, No Drawings

PROCESS FOR PREPARING N-ALKYL POLYHYDROXYALKYL AMINES IN AQUEOUS/HYDROXY SOLVENTS

CROSS-REFERENCE TO RELATED APPLICATION

This is a continuation of application Ser. No. 07/907,382, filed on Jul. 8, 1992 (now abandoned); which is a continuation-in-part of both application Ser. No. 07/736, 172, filed Jul. 26, 1991 (now abandoned), and application Ser. No. 07/820,712, filed Jan. 14, 1992 (Now U.S. Pat. No. 5,449,770).

FIELD OF THE INVENTION

The present invention relates to a chemical process for preparing N-alkyl polyhydroxyalkyl amines, especially ones having low nickel content and good color and odor characteristics, especially the reaction of N-alkylamines with reducing sugars and hydrogen in the presence of a nickel catalyst to prepare N-alkylamine polyols, and especially N-methylglucamine, suitable for use, e.g., in preparing fatty acid amide derivatives thereof useful as detersive surfactants.

BACKGROUND OF THE INVENTION

The manufacture of N-alkyl polyhydroxyalkyl amines (N-alkyl polyhydroxy amines), such as N-methylglucamine, has been known for many years, and such materials are available commercially. In the main, however, their use has been somewhat limited and such materials have been relatively expensive. Recently, there has been occasion to employ N-alkyl polyhydroxy amines, e.g., in reactions with fatty acid esters to prepare fatty acid polyhydroxy amide detersive surfactants for use in cleaning products. As can be imagined, were the cost of N-alkyl polyhydroxy amines to remain high, such laundry detergent use of the fatty acid polyhydroxy amide surfactants would be impractical. Accordingly, there is a continuing search for quick, inexpensive means for preparing N-alkyl polyhydroxy amines on a commercial scale.

Moreover, it is has been determined that care must be taken in preparing N-alkyl polyhydroxy amines in a form that is suitable for subsequent reaction with fatty acid methyl esters, since contamination of the N-alkyl polyhydroxy amines with, for example, hydrogenation catalysts such as Raney nickel, unreacted sugars, unreacted amine/sugar adduct, water, and the like, can seriously impact on the formation of the fatty acid polyhydroxy amide formation. For example, browning reactions, with the formation of undesirable color bodies, can occur. The formation of various undesirable by-products such as cyclic materials and/or esteramides can also occur. In a worse case scenario, by-product formation can be so high that the desired reaction of the N-alkyl polyhydroxy amine with the fatty acid methyl ester is essentially stopped in its entirety, with the formation of black, intractable tarry products.

The preparation of N-alkylamino polyols from N-alkylamines, sugars and hydrogen under the influence of nickel catalysis is a known process. However, the resulting N-alkylamino polyol reaction products, such as N-methyl glucamine, are typically contaminated with nickel catalyst and/or contain undesirable odoriferous or colored by-products. Contamination by nickel catalyst or by-products may be tolerable if the user can afford to purify the N-alkylamino polyol prior to use. However, the manufacturer of high volume, low-cost chemicals such as detersive surfactants can ill-afford raw materials which require expensive purification steps. For example, the manufacturer of surfactants which comprise polyhydroxy fatty acid amides (e.g., $C_{10}$–$C_{12}$ fatty acid amides of N-methyl glucamine or N-methyl fructamine) requires a source of N-alkylamino polyols which have desirable low color and low odor, as well as low nickel levels. Indeed, the manufacture of high quality polyhydroxy fatty acid amide surfactants relies heavily on having a source of such high quality, yet low-cost, N-alkylamino polyols.

The present invention solves the problem of nickel contamination, odor and undesirable coloration associated with the manufacture of N-alkylamine polyols. It thereby affords access to high quality polyhydroxy fatty acid amide surfactants. Moreover, the catalytic activity of the nickel catalyst used in the present process remains high over multiple reaction sequences, thereby allowing catalyst recycle with attendant, substantial cost savings.

The present invention provides simple means for preparing N-alkyl polyhydroxy amines, especially N-methylglucamine, in high yields, with low color formation, low ionic Ni content, and/or in a form that is particularly suited for, e.g., subsequent reaction with fatty acid esters, or use, either as is, or in quaternized form, as a cation.

BACKGROUND ART

A number of years ago, processes were explored for making textile assistants or detergents from fatty acids or their derivatives in combination with N-alkylglucamines, the latter made by reductive amination of glucose. Glucose reductive amination processes are more fully disclosed in U.S. Pat. No. 2,016,962, Flint et al., issued Oct. 8, 1935.

U.S. Pat. No. 1,985,424, Piggott, issued Dec. 25, 1934, discloses manufacturing "textile assistants" by reacting (a) the product of heating glucose and aqueous methylamine in presence of hydrogen and a hydrogenating catalyst under pressure with (b) an organic carboxylic acid such as stearic acid or oleic acid. The condensation product, prepared at about 160° C., is said to be "predominantly, if not exclusively, an amide" and is assertedly of the formula R—CO—$NR_1$—$CH_2$—$(CHOH)_4$—$CH_2OH$ wherein R is an alkyl radical containing at least 3 carbon atoms, while $R_1$ is hydrogen or an alkyl radical.

U.S. Pat. No. 2,016,962, issued Oct. 8, 1935, discloses a process for preparing glucamines and related products which involves, for example, reacting glucose, monomethylamine and hydrogen in the presence of water at temperatures around 100° C. The present invention provides a substantial improvement over the art-disclosed process, especially with regard to the quality of N-methyl glucamine produced.

U.S. Pat. No. 2,703,798, Schwartz, issued Mar. 8, 1955, asserts that compositions produced by reacting fatty acids or acid anhydrides with N-alkylglucamines (presumably such as the process as taught by Piggott) have poor color and poor detergency properties. It is indeed chemically reasonable that more than one compound can be formed by the Piggott process. Piggott makes no attempt to quantitatively prove the structures of the compounds or mixtures he prepared. Thus, Schwartz teaches problems associated with forming the condensation products of N-monoalkylglucamines and fatty acids, with respect to undesirable color characteristics and detergency properties.

Schwartz ('798) goes on to report an improvement as a result of reacting fatty ester (as distinct from fatty acid or anhydride) with N-alkylglucamines. Although this process may overcome one or another deficiency of the art, such as of Piggott, it now transpires that the Schwartz process still has difficulties, in particular, in that complex mixtures of compounds can be formed even by the Schwartz process. The reaction may take several hours and the process can fail to give high quality product. Neither the process of Piggott not the process of Schwartz is known to have ever borne fruit in commercial practice.

According to Schwartz, approximately equimolar proportions of N-monoalkylglucamines can be reacted with fatty alkyl esters by heating at 140° C.–230° C., preferably 160° C.–180° C. at normal, reduced or superatmospheric pressures for a period "somewhat in excess of one hour" during which time two initially immiscible phases merge to form a product said to be a useful detergent.

Suitable N-monoalkylglucamines are illustrated by N-methylglucamine, N-ethylglucamine, N-isopropylglucamine and N-butylglucamine. Suitable fatty alkyl esters are illustrated by the product of reacting a $C_6$–$C_{30}$ fatty acid with an aliphatic alcohol, e.g., methyl ester of lauric acid. Mixed glycerides of Manila oil or mixed glycerides of cochin coconut oil can apparently also be used as the fatty ester. When the glucamine is N-methylglucamine, the corresponding products with these fatty esters are characterized as the "fatty acid amides of N-methylglucamine," which are useful detergent surfactants. Another specific composition reported is assertedly "N-isopropylglucamine coconut fatty acid amide."

U.S. Pat. No. 2,993,887, Zech, issued Jul. 25, 1961, reveals there is even more complexity to the reactions of fatty substances with N-methylglucamine. In particular, Zech asserts that the products of high-temperature reactions (180° C.–200° C.) within the range disclosed by Schwartz have cyclic structures. No fewer than four possible structures are given. See '887 at column 1, line 63 to column 2, line 31.

According to Schwartz, supra, the products of the Schwartz process can be used for cleaning hard surfaces. According to Thomas Hedley & Co. Ltd. (now Procter & Gamble Ltd.), British Pat. No. 809,060 published Feb. 18, 1959, formula (I) compounds are useful as a surfactant for laundry detergents such as those having granular form. Hildreth (supra) mentions use of compounds of formula (I) in the biochemistry field as a detergent agent for solubilizing plasma membranes and EP-A 285,768, published Dec. 10, 1988, describes application of formula (I) compounds as a thickener. Thus, these compounds, or compositions containing them, can be highly desirable surfactants.

Yet another process for making compositions comprising formula (I) compounds is included in the above-identified disclosure of improved thickeners. See EP-A 285,768. See also H. Kelkenberg, Tenside Surfactants Detergents 25 (1988) 8–13, inter alia for additional disclosures of processes for making N-alkylglucamines which, along with the above-identified art-disclosed N-alkylglucamine processes can be combined with the instant process for an overall conversion of glucose and fatty materials to useful surfactant compositions.

The relevant disclosures of EP-A 285,768 include a brief statement to the effect that "it is known that the preparation of chemical compounds of formula (I) is done by reacting fatty acids or fatty acid esters in a melt with polyhydroxyalkylamines which can be N-substituted, optionally in the presence of alkaline catalysts." The above-referenced art strongly suggests that this statement is a gross oversimplification or is inaccurate. EP-A 285,768 does not cite any references in support of the quoted statement, nor has any reference other than EP-A 285,768 been found which actually does disclose any catalytic condensation of N-alkylglucamines with fatty esters or fatty triglycerides.

SUMMARY OF THE INVENTION

The present invention relates to a series of improvements relating to processes for preparing N-alkyl polyhydroxy amines (N-alkylamino polyols) by reacting an N-alkylamine with a reducing sugar (including reducing sugar derivatives) and hydrogen, either sequentially ("Adduct" Process) or simultaneously ("Glucose Addition" Process), preferably in the presence of a nickel catalyst, although other catalysts can be used. The improvements also include selection of the reducing sugar to minimize color bodies; treating the catalyst to maximize its performance; when the catalyst is nickel, operating under conditions to minimize solubilization of the nickel and/or reduce the level of soluble nickel; and selecting operating conditions which minimize side reactions which form undesirable products.

A. "Adduct" Process

In one aspect, the present invention encompasses a process (carried out under non-oxidizing conditions) for preparing N-alkyl polyhydroxy amines, comprising the steps of:

a) reacting a reducing sugar or reducing sugar derivative, preferably one that has a Gardner Color of less than about one, more preferably about water white (i.e., about Gardner 0, or like distilled water), with a primary amine at mole ratios of amine:sugar not greater than about 7:1, preferably less than about 2:1, and more preferably from about 1:1 to about 1.5:1, in an aqueous solvent, optionally mixed with, or replaced by, organic hydroxy solvent to provide an adduct, the reactants, if necessary, preferably having been deoxygenated (e.g., degassed by stripping with an inert gas, preferably nitrogen), said adduct formation preferably being carried out at a combination of temperature and time that will yield a Gardner Color of less than about 7, preferably less than about 4, and even more preferably less than about 1, said combination preferably being based upon a temperature of less than about 70° C., preferably less than 50° C., and even more preferably less than about 30° C., the typical temperature being from about 15° C. to about 20° C., especially for batch processes, the time typically being at least about one-half hour, preferably at least about one hour, for temperatures of about 30° C. or less and less than about ten minutes for temperatures of about 50° C. or more, to substantially reach a yield of said adduct which is at least about 90%, preferably at least about 95%, more preferably at least about 98%, based on the sugar reactant and preferably, at least for batch processes, said yield represents an equilibrium state of adduct formation, and said adduct being stable for at least 24 hours at 0° C.;

b) reacting said adduct from Step (a) with hydrogen under mild conditions, e.g., temperature of less than about 70° C., preferably less than about 65° C., more preferably less than about 60° C., at least initially, to achieve at least about 80%, preferably at least about 90%, more preferably at least about 95%, preferably followed by more stringent conditions, e.g., temperature of more than about 75° C. preferably more than about 80° C. up to about 135° C., said adduct preferably being substantially free from unreacted sugar starting material, in the presence of a catalyst, said adduct preferably not being admixed with any catalyst, especially nickel catalyst, more especially nickel catalyst that has been treated as disclosed hereinafter, for more than about an hour, more preferably not more than about one-half hour, before the hydrogen pressure is raised to at least about 500 psig, preferably at least about 1000 psig, more preferably at least about 1500 psig; and c) removing said catalyst and, preferably, but optionally, substantially removing the water, monoalkylamine, and/or organic hydroxy solvent in the reaction mixture, if required, to secure the N-alkyl polyhydroxy amine, all of said steps being preferably carried out under a reducing atmosphere ($H_2$) or at least under an inert atmosphere.

B. "Glucose Addition" Process

In another aspect, the present invention encompasses, in a process for preparing N-alkylamino polyols by reacting an N-alkylamine with a reducing sugar in the presence of a nickel catalyst under hydrogen pressure, the improvement which comprises:

a) removing substantially all oxides of nickel and, preferably, organic material, excess caustic, etc., from the nickel catalyst (conveniently, this can be done by washing the catalyst and/or contacting the nickel catalyst with hydrogen, typically under pressure and temperature of 50°–185° C. at 500–1,500 psig hydrogen);

(b) admixing the nickel catalyst from (a) with the N-alkylamine to provide mixture (b) under hydrogen pressure prior to admixture with the sugar;

(c) admixing the sugar with mixture (b) under hydrogen pressure;

(d) conducting the reaction of the sugar with the N-alkylamine/nickel catalyst mixture (b) at a temperature below about 80° C. and under hydrogen pressure (typically at least 100 psig, preferably at least 250 psig, more preferably at least 500 psig, and even more preferably at least 1000 psig) until at least about 80%, preferably at least about 90%, and even more preferably at least about 95%, by weight of the reducible compounds are no longer present in the reaction mixture;

(e) continuing the reaction, optionally at a temperature of up to about 120° C. (or 135° C.), until at least about 98.7%, preferably at least about 99.9% by weight of the reducible compounds are no longer present in the reaction mixture (the combination of steps (d) and (e) in this discussion is essentially the equivalent of steps (a) and (b) in the "Adduct" Process described hereinbefore); and (f) recovering the N-alkylamino polyol, preferably without purification (similar to (c) in the "Adduct" Process).

Preferably step (d) of the process is carried out at a temperature of from about 40° C. to about 70° C. Step (e) is preferably carried out at a temperature from about 80° C. to about 120° C.

The present invention, in both aspects A. and B., thus affords a process for the preparation of compounds which include, but are not limited to, N-alkyl glucamine, N-alkyl fructamine, N-alkyl maltamine or N-alkyl glycerol amine, the "Glucose Addition" process comprising the steps of:

(a) admixing a nickel catalyst, preferably as described hereinbefore and hereinafter, which is substantially free of oxides of nickel with an N-alkylamine (preferably N-methylamine);

(b) under hydrogen pressure, admixing an aqueous solution of glucose, fructose, maltose or glyceraldehyde, respectively, with the mixture from step (a);

(c) allowing the mixture from step (b) to react at a temperature of from about 40° C. to about 70° C. until at least about 95% by weight of the reducible compounds are no longer present in the reaction mixture; and (d) allowing the reaction from step (c) to continue at a temperature below about 120° C., and preferably at least about 80° C., until at least about 99.9% by weight of the reducible compounds are no longer present in the reaction mixture.

Preferably the process with glucose or fructose is conducted using nickel catalyst pre-treated with hydrogen to remove oxides of nickel, and wherein said catalyst is present at the 5% to 30%, preferably at least about 10%, level relative to sugar.

In typical processes herein, both "adduct" and "glucose addition," the nickel catalyst level is in the range of from about 5% to about 50%, most typically from about 5%, preferably from about 10%, to about 30%, by weight of the sugar reactants, for optimal throughput.

The invention also provides a process for preparing polyhydroxy fatty acid amide surfactants, comprising reacting a member selected from the group consisting of fatty acids, fatty acid anhydrides and fatty acid esters with an N-alkylamino polyol prepared according to the foregoing manner. In a preferred process, the fatty acid ester is a $C_{10}$–$C_{18}$ alkyl or alkenyl fatty acid methyl ester and the N-alkylamino polyol is selected from N-methyl glucamine, N-methyl fructamine, N-methyl maltamine and N-methyl glycerol amine.

C. Catalyst Optimization and Maintenance

In yet another aspect, the present invention relates to optimizing and maintaining the activity of the preferred nickel catalysts. Nickel catalysts, such as those that are commercially available, typically are contaminated with, e.g., oxides of nickel, organic materials, excess caustic, and/or alumina fines. The activity of the catalyst can be increased substantially by the reduction, or removal, of these impurities, even when they are present in very small amounts. Thus, washing with a solvent, or series of solvents, to remove organic materials and water-soluble inorganic materials to preferably lower the pH, and/or treatment with a strong reducing agent, e.g., hydrogen gas under high pressure and/or temperature conditions will improve and/or recover the activity of the nickel catalysts.

Surprisingly, it has been found that amine/reducing-sugar adduct and/or N-alkyl polyhydroxy amine solubilize nickel, especially at elevated temperatures, but that a combination of hydrogen gas and selected pressure/temperature conditions can reduce this solubilization and, in fact, reverse the process to deposit nickel and regenerate the catalyst. Lowering the soluble Ni content in the N-alkyl polyhydroxy amine product to less than about 10 ppm, preferably less than about 5 ppm, more preferably less than about 2 ppm, will effectively regenerate the catalyst.

In preferred processes herein, the sugar material is a reducing sugar, especially glucose, maltose, and/or galactose, and the amine compound is a member selected from the group consisting of $C_1$–$C_4$ alkyl or hydroxyalkyl amines. When the amine is monomethyl amine (hereinafter, simply "methyl amine") and the sugar is glucose, the preferred reaction product, N-methylglucamine, is secured.

DETAILED DESCRIPTION OF THE INVENTION

The processes of this invention employ reactants, catalysts and solvents which are known in the art. However, use of these materials in the manner disclosed herein provides superior reaction products. The following is intended to assist the manufacturer in the practice of the invention.

By "substantially free of nickel" herein is meant that the N-alkylamino polyol reaction product contains no more than about 20 parts per million (ppm) nickel, and preferably less than about 5 ppm nickel ($Ni^{++}$). Nickel can be conveniently measured by conventional atomic absorption spectroscopy, using diluted samples (5/1 dilution to minimize interference).

By "reducible compounds" or "reducibles" herein is meant chemical compounds which contain reducing sugars either in their natural state or as an adduct with the amine such as N-methylglucamine. Such compounds include, but are not limited to, species such as glucose, fructose, maltose, N-methylglucosylamine, N-methylfructosylamine, N-methyl-N-glucosylglucamine. This is measured by g.c. analysis.

By "g.c. analysis" herein is meant gas-liquid chromatography ("g.l.c.") using Hewlett-Packard 5890 Series 2 on column injection using DB1 15 meter 0.25µfilm thickness ID 250µ.

By "improved color" and/or "improved color stability" herein is meant the Gardner Color of the N-alkylamino reaction product, as produced by the present process. Moreover, the Gardner Color of the fatty amide derivatives which can be subsequently made therefrom is also substantially improved.

By "Gardner Color" herein is meant the standard Gardner measurement known in the art. A Gardner Color reading near zero (solution) represents a nearly colorless ("water-white") solution. Gardner Colors below about 7 are only marginally acceptable for the N-alkylamino polyol reaction products, and it is preferred to achieve Gardner Colors below about 4, preferably 0 to about 2. Of course, use of sugars having low Gardner Colors (e.g., 0 or 1, i.e., water-white syrups) will help ensure that N-alkylamino polyols having desirably low Gardner Colors will be produced. Stated otherwise, use of low (0–2) Gardner Color sugars (preferably white solids or water-white solutions) and use of the reaction sequence disclosed herein results in low Gardner Color N-alkylamino polyols (white or slightly off-white solids).

Gardner Color is determined by A.O.C.S. (American Oil Chemists Society) Official Method to 1a–64, entitled COLOR Gardner 1963 (Glass Standards) established 1978 and revised 1982. The equipment and standards for determining Gardner Color can be purchased from Delta Scientific, Box 5728, Long Island, N.Y. 20014, or from Gardner Laborator, Silver Spring, Md., U.S.A. As used herein, the Gardner Color limits typically refer to the color resulting from the color bodies that are present, or which are the result of the described reactions, and not to deliberately added color materials.

By "improved odor" herein is meant that the odor character of the reaction product is substantially free of amine or "fish" type odor (once any excess N-alkylamine is removed) and also substantially free of typical browning sugar odors.

By "nickel catalyst" herein is meant any of the conventional Raney nickel or "supported" nickel catalysts well-known in the art. Conventional nickel under the trademark RANEY NICKEL 4200 and 3200 (Grace Chemicals) are quite suitable for use herein. UCI (United Catalyst, Inc.) G-96B and G-49B and G-49C are also suitable. While not intending to be limited by theory, it is believed that removing oxides of nickel from the catalyst prevents or impedes dissolution of nickel ions into the reaction milieu, and thus results in the formation of reaction products having a desirable low nickel content. Moreover, it has been found that the nickel catalyst pre-treated and preferably post-treated with pressurized hydrogen can be re-used in multiple subsequent reactions, thereby yielding a substantial overall cost savings.

By "pressurized hydrogen" or "hydrogen pressure" herein is meant: for treatment of the nickel catalyst the pressure typically is from about 10.0 (preferably about 500) psig to about 5,000 (preferably about 3500) psig; for reaction step c-d of the "glucose addition" process and step (b) of the "adduct" process, typically from about 100 (preferably about 200, more preferably about 500) psig to about 5,000 (preferably about 3500) psig.

By "sugars" herein is meant reducing sugars such as glucose, fructose, mannose, lactose, maltose, xylose and the like. The term "sugars" herein also includes glyceraldehyde. Such "sugars" include plant syrups such as cane syrups, corn syrups, potato starch-derived sugar syrups, hydrolyzed wood pulp-derived sugars and the like. High fructose, high glucose and high maltose syrups are economical and preferred, especially if their Gardner Color is satisfactory.

By "N-alkylamines" herein is meant compounds such as the N-methyl, N-ethyl, N-propyl, etc., $C_1$–$C_{10}$ N-alkylamines, the corresponding hydroxy-substituted amines, e.g., ethanolamine. The $C_1$–$C_3$ alkylamines are preferred, and N-methylamine is most preferred.

A. "Adduct" Process

In the first aspect, the process involves pre-reacting the amine and reducing sugar to form an adduct. This process helps minimize the contact between the reducing sugar and the catalyst when the hydrogen pressure is low, thus avoiding the need to have the reactor under high pressure when the sugar is introduced to the reactor.

The reaction for the preparation of the polyhydroxyamines herein can be termed the "R-1" reaction, and is illustrated by the formation of N-methylglucamine, wherein $R^1$ is methyl.

water and/or organic solvent, e.g., methanol $R^1NH_2$ +glucose→Adduct+$H_2O$

The Adduct has the formula:

$$R^1NH-CH-(CHOH)_3-CH-CH_2OH \quad \text{(I)}$$
(with O bridging the two CH groups)

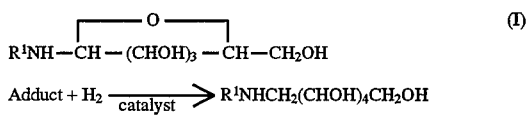

The reactants, solvents and catalysts used in the R-1 reaction are all well-known materials which are routinely available from a variety of commercial sources. The following are nonlimiting examples of materials which can be used herein.

Amine Material

The amines useful in all of the R-1 reaction herein are primary amines of the formula $R^1NH_2$, wherein $R^1$ is, for example, alkyl, e.g., $C_1$–$C_{18}$, especially $C_1$–$C_4$ alkyl, or the corresponding hydroxyalkyls, e.g., $C_1$–$C_4$ hydroxyalkyl. Examples include methyl, ethyl, propyl, hydroxyethyl, and the like. Nonlimiting examples of amines useful herein include methyl amine, ethyl amine, propyl amine, butyl amine, 2-hydroxypropyl amine, 2-hydroxyethyl amine; methyl amine is preferred. All such amines are jointly referred to herein as "N-alkyl amines." The amine can be either anhydrous or in a solvent, e.g., aqueous solvent, of a concentration of from about 30% to about 90%, preferably from about 40% to about 70%.

Polyhydroxy Material

A preferred source of polyhydroxy materials useful in all of the R-1 reactions herein comprise reducing sugars or reducing sugar derivatives. A particular advantage of the present "Adduct" process is that it can be carried out in the presence of water in Step (a). Accordingly, raw materials such as corn syrup, and the like, can be used as the sugar source. However, the sugar solution can be prepared from granular, powdered, etc., sugar by dissolving the sugar in the solvent, preferably aqueous solvent. Concentrations of sugar in the solvent, e.g., water, are typically from about 40% to about 90%, preferably from about 50% to about 70% (Typically, 71% is the upper limit.) It is highly important that the color of the starting sugar material for all be less than about one on the Gardner Color scale, preferably less than about Gardner 0+, and more preferably about water white. Typical color materials that are present in the starting sugar materials negatively affect the catalyst described hereinafter, and the reaction yield. These color materials also contribute to the eventual color of the N-alkyl polyhydroxy amine. Such colors can be removed, if present, by procedures such as "carbon bleaching," in which the color materials are adsorbed. The sugar material is preferably handled without excessive heating and/or under non-oxidizing conditions to prevent degradation.

More specifically, reducing sugars useful herein include glucose (preferred), maltose (preferred), fructose, maltotriose, xylose, galactose (preferred), lactose, and mixtures thereof.

Catalyst

A variety of hydrogenation catalysts can be used in the R-1 reaction. Included among such catalysts are nickel (preferred), platinum, palladium, iron, cobalt, tungsten, various hydrogenation alloys, and the like. The catalyst used in Step (b) is preferably a particulate nickel catalyst, Raney nickel, nickel, other nickel catalysts affixed to substrate materials such as silica or alumina. Catalysts which are easier to remove (e.g., by filtration) in Step (c) of the process are preferred. Highly preferred catalysts herein comprise "United Catalyst G49B," "United Catalyst G96," and "UCI C46" particulate Ni catalysts supported on silica, available from United Catalysts, Inc., Louisville, Ky., and Raney nickel type catalysts from W. R. Grace & Co., of Baltimore, Md., such as RA4200 and RA3100.

Solvent

Formation of the adduct in the R-1 process is conveniently carried out in water and/or organic solvent, especially polar, most preferably hydroxy solvents. Typical examples of organic solvents useful herein in the formation of the amine-sugar adduct include methanol (preferred), ethanol, 1-propanol, iso-propanol, the butanols, ethylene glycol, 1,2-propylene glycol (preferred), 1,3-propylene glycol, glycerol and the like. The amine itself can also function as a solvent, typically at mole ratios of amine:sugar of from about 4:1 to about 30:1.

The hydrogenation reaction of the R-1 reaction can also be carried out in the presence of an organic or aqueous solvent which dissolves the adduct. Hydrogenation solvents are, conveniently, polar, especially hydroxy, solvents, i.e., of the same type as those mentioned above for use in the formation of the adduct. When substantially anhydrous organic solvent is used, the unreacted amine is removed with the water after Step (a). However, when an aqueous solvent is used, the amine and solvent are not removed until Step (c).

Methanol is a preferred organic solvent for use in the hydrogenation reaction.

General R-1 Reaction Conditions

Reaction conditions for the R-1 reaction are as follows.

Step (a) Adduct formation

Step (a) of the process is preferably carried out at a temperature of from about 0° C. to about 80° C., preferably from about 10° C. to about 60° C., for processes utilizing organic hydroxy solvent and below about 70° C., preferably less than about 50° C., more preferably less than about 30° C., more preferably from about 15° C. to about 25° C., for aqueous solvents.

The reaction time used for adduct formation will typically be on the order of from a few minutes to about 20 hours, depending somewhat on the reaction temperature chosen and/or the ratio of amine to sugar. In general, for the organic solvent, lower reaction temperatures in the range of 0° C.–80° C. require longer reaction times, and vice-versa. In general, for the organic solvent, over a preferred 10° C.–60° C. reaction temperature range, good adduct yields, e.g., more than about 90%, preferably more than about 95%, are achieved in 1–10 hours for the organic solvent. For the lower reaction temperature range, 0°–70° C., preferably 0°–30° C., that gives good color, especially in water, the reaction time can also be as much as 10 hours, but, typically, equilibrium is substantially reached within about four hours or less, especially with higher amine:sugar ratios. The temperature and reaction time are selected to give an adduct with a Gardner Color of less than about 7, preferably less than about 4, more preferably less than about 1. Good adduct color is necessary for obtaining good reactions and color in any subsequent hydrogenation reaction and maintaining catalyst activity. Above a Gardner Color of about 7, the color bodies will actually interfere with the hydrogenation reaction. Below a Gardner Color of about 4 (preferably below about 1), the resulting N-alkyl polyhydroxy amine has good color. The color bodies can be removed by, e.g., carbon bleaching as used for the sugar solution.

The adduct also has a very low level of glucose. Typically, the glucose level, as a percentage of the adduct is less than about 2%, preferably less than about 1%, and more preferably less than about one-half of one percent. Glucose interferes with the hydrogen reaction step to form the N-alkyl polyhydroxy amine. Excess amine can also help reduce the glucose level and minimize formation of sorbitol during hydrogenation.

In general, the temperature will rise during adduct formation since the reaction is exothermic. Therefore, maintaining temperatures below about 30° C., as required in batch processes, involves providing cooling for the reactants and/or the reaction mix. Temperatures above about 50° C. require reaction times of less than about 10 minutes to avoid excessive color formation. Such short times are normally not feasible except in a continuous reaction. Even with such a continuous reaction, back-mixing should be minimized, e.g., by use of plug flow conditions to avoid excessive exposure of the adduct to higher temperatures. Ideally, the adduct is promptly reacted with hydrogen to form the corresponding N-alkyl polyhydroxy amine to minimize degradation. However, temperatures below about 30° C., preferably less than about 20° C., allow one to handle and/or store the adduct for at least several hours, which facilitates the use of batch processes. At 0° C., the adduct is stable for 24 hours.

Surface temperatures, e.g., when preheating the adduct for the hydrogen reaction process, should be maintained below about 100° C., preferably below about 70° C.

Reactant concentrations can vary. Molar ratios of amine:sugar not greater than about 7:1 are preferably used herein, although ratios up to about 30:1 can be used when the amine is used as a solvent, at least in part. Generally good adduct formation is achieved at about a 1:1 mole ratio of amine:sugar; some slight excess of amine is preferably used, e.g., mole ratios of 1.05:1; 1.1:1; 1.5:1; 2:1, and the like. Typical reactant concentrations in the water and/or hydroxy solvent are in the 10–80%, typically 40–70% (wt.) range. Adduct formation can be carried out at atmospheric or super-atmospheric pressures.

Step (b) Reaction with Hydrogen

Step (b) should be accomplished so as to avoid the prolonged exposure of the adduct to the catalyst when the hydrogen pressure is less than about 500 psig, and preferably the hydrogen pressure should be at least about 1000, and more preferably at least about 1500 psig. Keeping this time below about one hour, and preferably below about a half hour, minimizes the amount of catalyst metal, e.g., nickel, that is converted to water soluble ion. Such ions are undesirable for a variety of reasons including their affect on color formation and the limits on such materials that are incompatible with other materials, safety, etc.

Step (b) can be carried out in either a slurry process or a fixed bed. Step (b) is preferably carried out at a temperature of from about 20° C. to about 120° C., preferably from about 50° C. to about 100° C. for organic hydroxy solvent processes. Step (b) is preferably carried out in two stages for aqueous solvent processes. The first stage is at a temperature that is low enough to avoid formation of the corresponding reduced sugar, e.g., sorbitol in the case of glucose, and other unwanted byproducts. Typically this is from about 20° C. to about 70° C., more preferably from about 40° C. to about 65° C., and even more preferably from about 50° C. to about 60° C. In the second stage, after the reduction (hydrogenation) of the adduct to the N-alkyl polyhydroxy amine is at least about 80%, preferably at least about 90%, more preferably at least about 95%, complete, the temperature is raised to at least about 75° C., preferably at least about 80° C., and up to about 135° C., preferably 130° C., so that the remaining adduct and any other materials that may form color bodies are minimized and the adduct is at least about 95%, preferably at least about 98%, more preferably at least about 99.9% converted to the corresponding N-alkyl amino polyol. This second stage is essential to the preparation of N-alkyl polyhydoxy arline with good stable color upon heating.

During Step (b) it is highly preferred to avoid localized overheating, e.g., at the surface of the heating element or heat exchanger. Such surface of "skin" temperatures should be below about 180° C., preferably below about 100° C., and even more preferably less than about 70° C., during the first stage and less than about 100° C. during the second stage.

The reaction with hydrogen is preferably carried out with limited initial water when the solvent is an organic hydroxy solvent, although even then, water (e.g., up to 1:1 wt. $H_2O$:alcohol) can be present. Optional water removal from the adduct prepared in Step (a) can be effected by use of drying agents, or by simply stripping water and solvent from the adduct, and then redissolving the adduct in fresh water-free solvent. The hydrogen reaction can typically be run, for example, at temperatures of 20° C.–120° C. at 50–1,000 psi or, for example, at 50° C.–90° C. at 100–500 psi for periods of 0.1–35 hours, generally 0.5–8 hours, typically 1–3 hours when the organic solvent is used.

When the solvent comprises water, as discussed before, the hydrogenation reaction is done in two stages, the first being at a temperature between about 20° C. and about 70° C., preferably from about 40° C. to about 65° C., more preferably from about 50° C. to about 60° C., and the second stage being at a temperature above about 75° C., preferably above about 80° C., up to about 135° C.

The adduct/solvent solution used in the hydrogen reaction is typically at a 10–80%, typically 40–70%, (wt.) solute level.

It will be appreciated that the selection of hydrogen reaction conditions will depend somewhat on the type of pressure equipment available to the formulator, so the above-noted reaction conditions can be varied without departing from this invention. However, as noted before, the hydrogen pressure preferably should be above about 500, preferably 1000, more preferably about 1500, psig when the adduct and the catalyst, especially the preferred nickel catalyst, are both present. Use of lower pressures down to about 100 psig will require either a separate step to remove Ni ion, or more prolonged post treatment, as discussed hereinafter, to achieve very low Ni content.

Hydrogen reaction catalyst levels are typically from about 1% to about 100%, preferably from about 2% (preferably about 5%) to about 30% (preferably 20%) more preferably from about 5% (preferably 10%) to about 15% (preferably about 20%) solids by weight, calculated based on wt. catalyst:wt. reducing sugar substituent. The product of Step (b) is preferably dried by solvent/water stripping, or by crystallization or by means of effective drying agents. This helps prevent reversion to the sugar starting material.

With regard to Step (b), it is preferred that the adduct be substantially free from interfering amounts of unreacted amine starting material when organic solvent is used. While not intending to be limited by theory, it appears that such amines can undesirably affect the reaction with hydrogen, perhaps by modifying the surface, of the metal catalyst, especially the preferred substrate-supported metal catalysts used herein. Whatever the mechanism, it is preferred that levels of unreacted amine be kept low, although a few percent (e.g., below about 20 weight percent of the adduct) can be present, assuming the formulator is willing to adjust levels of metal catalyst according to need. In any event, removal of unreacted amine to provide the adduct in a form substantially free from interfering amounts of unreacted amine prior to the reaction with hydrogen is a straightforward matter, especially with volatile amines such as methyl amine. Thus, vacuum or heat stripping of the amine can be employed. Indeed, in the Examples I–VI hereinafter the unreacted amine is automatically removed when the solvent and water are stripped from the adduct prior to the reaction with hydrogen. Or, the reaction stoichiometry can be such that the amount of residual, unreacted amine is of little consequence to the subsequent hydrogen reaction step.

Steps (a)–(c) of the R-1 process are preferably conducted under non-oxidizing conditions (e.g., $H_2$ or inert gas) to provide good color. Catalyst removal is done preferably under hydrogen pressure to prevent Ni (catalyst) dissolution or at least under inert conditions.

The compounds prepared herein can be used in an overall process for preparing polyhydroxy fatty acid amide surfactants which includes, e.g., an amide-forming reaction comprising reacting the N-alkyl polyhydroxy amine materials prepared in the foregoing manner with, e.g., fatty acid esters in an organic hydroxy solvent in the presence of base catalyst. The formation of such surfactants with high purity and low color is an especially beneficial result of such a process when an organic hydroxy solvent is used, since the detergent formulator can pump and/or incorporate the polyhydroxy fatty acid amide reaction product plus the reaction solvent such as 1,2-propylene glycol, glycerol, or alcohol (e.g., in liquid detergents) directly into the final detergent formulation. This offers economic advantages in that a final solvent removal step is rendered unnecessary, particularly where anhydrous glycols or ethanol are used.

B. The "Glucose Addition" Process

The process utilizing glucose addition after premixing the catalyst and amine is a simplified reaction which can achieve good results so long as the glucose is added under a hydrogen pressure of at least about 100 psig, preferably at least about 500 psig, and more preferably at least about 1000 psig, at a temperature of less than about 80° C., preferably less than about 70° C., most preferably less than about 60° C.

The preparation of the N-alkylaminol polyols by the present processes can be conducted in any well-stirred pressure vessel suitable for conducting hydrogenation reactions. In a convenient mode, for the "Glucose Addition" process, a pressure reactor with a separate storage reservoir is employed. The reservoir (which, itself, can be pressurized) communicates with the reactor via suitable pipes, or the like. In use, a stirred slurry of the nickel catalyst is first "cleaned," including being treated with hydrogen to remove traces of nickel oxides. This can be conveniently done in the reactor. (Alternatively, if the manufacturer has access to an oxide-free source of nickel catalyst, pretreatment with $H_2$ is unnecessary. However, for most manufacturing processes some trace of oxides will inevitably be present, so the $H_2$ treatment is preferred.) After removal of excess slurry medium (water) the N-alkyl amine is introduced into the reactor, as disclosed in Example XIII. Thereafter, the sugar is introduced from the storage reservoir into the reactor either under hydrogen pressure or by means of a high pressure pumping system, and the reaction is allowed to proceed. The progress of the reaction can be monitored by periodically removing samples of the reaction mixture and analyzing for reducibles using gas chromatography ("g.c."), or by heating the sample to about 100° C. for 30–60 minutes in a sealed vial to check for color stability. Typically, for a reaction of about 8 liters (ca. 2 gallons) size the initial stage (to 95% of reducibles being depleted) requires about 60 minutes, depending somewhat on catalyst level and temperature. The temperature of the reaction mixture can then be raised to complete the reaction (to 99.9% of the reducibles being depleted).

C. Nickel Catalyst Optimization and Maintenance

The nickel catalysts discussed hereinbefore are preferably free of catalytic activity inhibiting quantities of nickel oxides, organic materials, caustic, alumina fines, etc. In general, commercially available nickel catalysts will not have optimum activity, especially after shipping and/or storage. Therefore, it is desirable to wash the catalyst with one, or more, solvents to effect removal of organics and/or water-soluble materials and/or treatment of the catalyst to destroy, or remove, the nickel oxides. Once the catalyst is "cleaned," the catalyst is desirably maintained under non-reactive atmosphere, e.g., nitrogen gas, or, more desirably, a reducing gas, e.g., hydrogen. Any exposure to the normal atmosphere should desirably occur for only short periods of time and while the temperature is low.

When the nickel catalyst is in contact with either adduct or N-alkyl polyhydroxyalkyl amine, the hydrogen pressure should be maintained to minimize catalyst solubilization. Similarly, a high hydrogen pressure, e.g., from about 100 psig to about 3500 psig, preferably from about 500 psig to about 1500 psig, and a temperature of from about 20° C. to about 135° C., preferably from about 40° C. to about 85° C., will reduce the level of nickel ion dissolved in the N-alkyl polyhydroxyalkyl amine, and, by depositing the nickel back onto the catalyst, regenerate its activity.

When the catalyst is separated from the N-alkyl polyhydroxyalkyl amine, the temperature should be less than about 135° C., preferably less than about 85° C., and the separation, typically filtration, should be accomplished under hydrogen pressure.

Regeneration of catalyst can be achieved using the step described for initial activation.

All percentages, ratios and proportions herein are by weight, unless otherwise specified. All limits and numerical values herein are approximate unless otherwise stated.

ORGANIC SOLVENT EXAMPLES (I–VIII)

Example I

A typical R-1 reaction is as follows.

A reaction mixture comprising methyl amine (10.73 g; 40% solution in $H_2O$; Aldrich), glucose (25 g) and ethanol (100 mls) is prepared at room temperature, allowed to stand overnight and is boiled away at 40° C. on a rotary evaporator to provide a solid adduct. 21.56 g of the adduct are admixed with 110 mls methanol and 2 g of United Catalyst G49B in a rocking autoclave and hydrogenated at 50° C. for 28 hours at about 250 psi hydrogen. The reaction product is then removed from the rocking autoclave and hot filtered through a glass microfibre filter (Whatman, 934-AH) to remove nickel. (A slight yellowish/greenish tinge to the solution/product can indicate the presence of trace amounts of nickel; final traces of nickel can be removed by, for example, filtration through neutral silica gel or bleaching earth). The N-methylglucamine can be recovered as a substantially white solid, e.g., by evaporating the methanol, preferably with reduced heat (below 60° C.) under vacuum. The product is in a form suitable for any desired use; it is particularly suitable for reaction with fatty acid esters to provide fatty acid polyhydroxy amides.

Example II

An R-1 reaction using corn syrup as a reactant is as follows.

Corn syrup (28.75 g, 71% in water, 99% glucose composition, Cargill), 75 mls of methanol (anhydrous) and 2.0 g of Ni catalyst (G49B, United Catalyst) are charged to an autoclave glass liner. The glass liner is placed into the rocking autoclave. The reaction mixture is purged twice with 200 psig $N_2$ and once with 200 psig $H_2$. Next, the reaction mixture is charged with 250–259 psig $H_2$ and the reaction heated to 60° C. for 1 hour. Methylamine (28 mls; 8.03 molar in ethanol; Fluka Chemicals) is charged to the reactor under pressure. The reaction is continued for 7 hours at 60° C. then cooled to room temperature. At room temperature, the reaction solidifies in the reactor and the filtrate is removed directly from the reactor (which contains an internal filter) under pressure. The catalyst thus remains in the reactor. The filtrate is colorless and is dried down to give 2.91 grams of product. The reactor is charged with methanol (50 mls) and heated to 60° C. for 2 hours, at which time the first wash is recovered. Another 50 mls methanol is added to reactor and heated at 70° C. for 30 minutes, at which time second wash is removed from reactor. Wash 1 and 2 are combined and dried down to give 17.55 grams of N-methylglucamine product. The dried product is essentially colorless and can be used in an "R-2" reaction to give colorless R-2 product such as lauroyl N-methylglucamide, as described below.

The polyhydroxyamine products of the aforesaid R-1 reaction, preferably with water substantially removed, are desirable and can be further employed in an amide-forming reaction which is designated herein as the "R-2" reaction. A typical R-2 amide-forming reaction herein can be illustrated by the formation of lauroyl N-methyl glucamide, as follows:

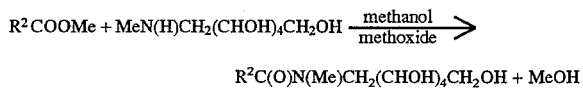

wherein R is $C_{11}H_{23}$ alkyl.

Thus, the Examples herein encompass an overall process for preparing polyhydroxy fatty acid amide surfactants, all as noted above for the R-1 process, comprising:

(a) reacting a reducing sugar or reducing sugar derivative with an amine in an organic hydroxy solvent (preferably, methanol) to provide an adduct;

(b) reacting said adduct from Step (a) (preferably, as noted above, free from interfering amounts of unreacted amine starting material) dissolved in said solvent (preferably, methanol) with hydrogen in the presence of a catalyst;

(c) removing said catalyst and substantially removing water from the reaction mixture to provide the polyhydroxyamine reaction product; and, thereafter, per the R-2 process;

(d) reacting said substantially anhydrous polyhydroxyamine product from Step (c) with a fatty acid ester in an organic hydroxy solvent (preferably, methanol) in the presence of a base catalyst to form the polyhydroxy fatty acid amide surfactant (preferably, at a temperature below about 100° C.); and (e) optionally, removing said solvent used in Step (d).

More specifically, the combination of R-1 and R-2 reactions herein provides an overall process (R-1 plus R-2) which can be used to prepare polyhydroxy fatty acid amide surfactants of the formula:

wherein: $R^1$ is H, $C_1$–$C_4$ hydrocarbyl, 2-hydroxyethyl, 2-hydroxy propyl, or a mixture thereof, preferably $C_1$–$C_4$ alkyl, more preferably $C_1$ or $C_2$ alkyl, most preferably $C_1$ alkyl (i.e., methyl); and $R^2$ is a $C_5$–$C_{31}$ hydrocarbyl moiety, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; and Z is a polyhydroxyhydrocarbyl moiety having a linear hydrocarbyl chain with at least 3 hydroxyls directly connected to the chain, or an alkoxylated derivative (preferably ethoxylated or propoxylated) thereof. Z preferably will be derived from a reducing sugar in a reductive amination reaction; more preferably Z is a glycityl moiety. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —$CH_2$—$(CHOH)_n$—$CH_2OH$, —$CH(CH_2OH)$—$(CHOH)_{n-1}$—$CH_2OH$, —$CH_2$-$(CHOH)_2(CHOR')(CHOH)$—$CH_2OH$, where n is an integer from 3 to 5, inclusive, and R' is H or a cyclic mono- or poly- saccharide, and alkoxylated derivatives thereof. Most preferred are glycityls wherein n is 4, particularly —$CH_2$—$(CHOH)_4$—$CH_2O$.

In Formula (I), $R^1$ can be, for example, N-methyl, N-ethyl, N-propyl, N-isopropyl, N-butyl, N-isobutyl, N-2-hydroxy ethyl, or N-2-hydroxy propyl.

$R^2$—CO—N< can be, for example, cocamide, stearamide, oleamide, lauramide, myristamide, capricamide, palmitamide, tallowamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The following reactants, catalysts and solvents can conveniently be used in the R-2 reaction herein, and are listed only by way of exemplification and not by way of limitation. Such materials are all well known and are routinely available from a variety of commercial sources.

Reactants

Various fatty esters can be used in the R-2 reaction, including mono-, di- and tri-esters ( i.e., triglycerides). Methyl esters, ethyl esters, and the like are all quite suitable. The polyhydroxyamine reactants include reactants available from the above-described R-1 reaction, such as N-alkyl and N-hydroxyalkyl polyhydroxyamines with the N-substituent group such as $CH_3$—, $C_2H_5$—, $C_3H_7$—, $HOCH_2CH_2$—, and the like. (Polyhydroxyamines available from the R-1 reaction are preferably not contaminated by the presence of residual amounts of metallo hydrogenation catalysts, although a few parts per million [e.g., 10–20 ppm] can be present.) Mixtures of the ester and mixtures of the polyhydroxyamine reactants can also be used.

Catalysts

The catalysts used in the R-2 reaction are basic materials such as the alkoxides (preferred), hydroxides (less preferred due to possible hydrolysis reactions), carbonates, and the like. Preferred alkoxide catalysts include the alkali metal $C_1$–$C_4$ alkoxides such as sodium methoxide, potassium ethoxide, and the like. The catalysts can be prepared separately from the reaction mixture, or can be generated in situ using an alkali metal such as sodium. For in situ generation, e.g., sodium metal in the methanol solvent, it is preferred that the other reactants not be present until catalyst generation is complete. The catalyst typically is used at a level of about 5 mole % of the ester reactant. Mixtures of catalysts can also be used.

Solvents

The organic hydroxy solvents used in the R-2 reaction include, for example, methanol, ethanol, propanol, isopropanol, the butanols, glycerol, 1,2-propylene glycol, 1,3-propylene glycol, and the like. Methanol is a preferred alcohol solvent and 1,2-propylene glycol is a preferred diol solvent. Mixtures of solvents can also be used.

General R-2 Reaction Conditions

It is an objective herein to prepare the desired products while minimizing the formation of cyclized by-products, ester amides and color bodies. Reaction temperatures below about 135° C., typically in the range of from about 40° C. to about 100° C., preferably 50° C. to 80° C., are used to achieve this objective, especially in batch processes where reaction times are typically on the order of about 0.5–2 hours, or even up to 6 hours. Somewhat higher temperatures can be tolerated in continuous processes, where residence times can be shorter.

The following examples are intended to illustrate the practice of the R-2 reaction using the N-polyhydroxyamines prepared by the above-disclosed R-1 reaction (with $H_2O$ having been removed), but are not intended to be limiting thereof. It is pointed out that the concentration ranges of the reactants and solvent in Example III provide what can be termed a "70% concentrated" (with respect to reactants) reaction mixture. This 70% concentrated mixture provides excellent results, in that high yields of the desired polyhydroxy fatty acid amide product are secured rapidly. Indeed, indications are that the reaction is substantially complete within one hour, or less. The consistency of the reaction mixture at the 70% concentration level provides ease of handling. However, even better results are secured at the 80% and 90% concentration levels, in that chromatography data indicate that even less of the undesired cyclized by-products are formed at these higher concentrations. At the higher concentrations the reaction systems are somewhat more difficult to work with, and require more efficient stirring (due to their initial thickness), and the likes at least in the early stages of the reaction. Once the reaction proceeds to any appreciable extent, the viscosity of the reaction system decreases and ease of mixing increases.

Example III

A reaction mixture consisting of 84.87 g fatty acid methyl ester (source: Procter & Gamble methyl ester CE1270), 75 g N-methyl-D-glucamine (source: Example I, above), 1.04 g sodium methoxide (source: Aldrich Chemical Company 16,499-2) and 68.51 g methyl alcohol (30% by wt. of reaction mixture) is used. The reaction vessel comprises a standard reflux set-up fitted with a drying tube, condenser and stir bar. In this procedure, the N-methylglucamine is combined with methanol with stirring under argon and heating is begun with good mixing (stir bar; reflux). After 15–20 minutes, when the solution has reached the desired temperature, the ester and sodium methoxide catalyst are added. Samples are taken periodically to monitor the course of the reaction, but it is noted that the solution is completely clear by 63.5 minutes. It is judged that the reaction is, in fact, nearly complete at that point. The reaction mixture is maintained at reflux for 4 hours. The recovered reaction mixture weighs 156.16 grams. After vacuum drying, an overall yield of 106.92 grams of granular purified product is recovered, which can easily be ground into smaller particles. However, percentage yields are not calculated on this basis, inasmuch as regular sampling throughout the course of the reaction makes an overall percentage yield value meaningless.

Example IV

An overall process at the 80% reactant concentration level for the amide synthesis is as follows.

A reaction mixture consisting of 84.87 g fatty acid methyl ester (source: Procter & Gamble methyl ester CE1270), 75 g N-methyl polyhydroxyamine per Example II, above, 1.04 g sodium methoxide and a total of 39.96 g methyl alcohol (ca. 20% by wt. of reaction mixture) is used. The reaction vessel comprises a standard reflux set-up fitted with a drying tube, condenser and mechanical stirring blade. The N-methylglucamine/methanol is heated with stirring under argon (reflux). After the solution has reached the desired temperature, the ester and sodium methoxide catalyst are added. The reaction mixture is maintained at reflux for 6 hours. The reaction is essentially complete in 1.5 hours. After removal of the methanol, the recovered product weighs 105.57 grams. Chromatography indicates the presence of only traces of undesired ester-amide by-products, and no detectable cyclized by-product.

Example V

The process of Example IV is repeated at the 90% reactant level for the polyhydroxy fatty acid amide synthesis step. Levels of undesirable by-products are extremely low, and reaction is essentially complete at 30 minutes. In an alternate mode, the reaction can be initiated at a 70% reactant concentration, methanol can be stripped during the course of the reaction and the reaction taken to completion.

Example VI

The process of Example III is repeated in ethanol (99%) and 1,2-propylene glycol (essentially dry), respectively, with good product formation. In an alternate mode, a solvent such as 1,2-propylene glycol is used in the R-2 step, with methanol stripping throughout the process. The resulting surfactant/glycol mix can be used directly in a detergent composition.

While the foregoing disclosure generally relates to a solvent-assisted method for preparing N-methyl polyhydroxy amines, such as N-methylglucamine, as well as their fatty acid amide derivatives using fatty methyl esters, it is to be understood that variations are available which do not depart from the spirit and scope of this invention. Thus, reducing sugars such as fructose, galactose, mannose, maltose and lactose, as well as sugar sources such as high dextrose corn syrup, high fructose corn syrup and high maltose corn syrup, and the like, can be used to prepare the polyhydroxyamine material (i.e., to replace glucamine) of the reaction. Likewise, a wide variety of fats and oils (triglycerides) can be used herein in place of the fatty esters exemplified above. For example, fats and oils such as soybean oil, cottonseed oil, sunflower oil, tallow, lard, safflower oil, corn oil, canola oil, peanut oil, fish oil, rapeseed oil, and the like, or hardened (hydrogenated) forms thereof, can be used as the source of triglyceride esters for use in the present process. It will be appreciated that the manufacture of detersive surfactants from such renewable resources is an important advantage of the present process. The present process is particularly useful when preparing the longer-chain (e.g., $C_{18}$) and unsaturated fatty acid polyhydroxy amides, since the relatively mild reaction temperatures and conditions herein afford the desired products with minimal by-product formation. A pre-formed portion of the polyhydroxy fatty acid amide surfactant can be used to assist initiation of the R-2 amide-forming reaction when triglycerides or the longer-chain methyl esters are used as reactants. It has further been determined that surfactant yields in the R-2 process can be increased by simply storing the solidified product (which contains some minor amount of entrained solvent and reactants) e.g., at 50° C., for a few hours after removal from the reaction vessel. Storage in this manner apparently allows the last fraction of unreacted starting materials to continue to form the desired polyhydroxy fatty acid amide surfactant. Thus, yields can be increased appreciably, which is an important consideration in large-scale industrial processes.

The following illustrates the use of the above-described surfactant products of the overall R-1 plus R-2 process to prepare fully-formulated detergent compositions. The examples are not intended to be limiting, since a wide variety of surfactants, builders and optional detersive adjuncts and other ingredients well-known to detergent formulators can be used in such compositions, all at conventional usage levels.

Example VII

A typical powdered laundry detergent composition is prepared using standard procedures, as follows:

| Ingredient | Percent (wt.) |
| --- | --- |
| Coconut N-methylglucamide* | 8.0 |
| $C_{12}$–$C_{14}$ alkyl benzene sulfonate, Na salt | 9.0 |
| Sodium sulfate | 10.0 |
| Zeolite A (1–10 micron size) | 30.0 |
| Sodium carbonate | 30.0 |
| Brightener | 1.0 |
| Optional perfumes and minors | 3.0 |
| Residual moisture | Balance |

*Prepared in 1,2 propylene glycol, with methanol stripping per Example VI; resulting mix of surfactant/glycol is added to the detergent composition; fatty acids derived from $C_{12}$–$C_{14}$ coconut oil.

Example VIII

A typical liquid laundry detergent composition is as follows.

| Ingredient | Percent (wt.) |
| --- | --- |
| Coconut N-methylglucamide* | 15.0 |
| $C_{12}$–$C_{14}$ fatty acid | 3.0 |
| Citric acid | 3.0 |
| Monoethanolamine | 2.5 |
| Ethanol | 3.5 |
| $C_{14}$–$C_{15}$ alkyl ethoxylate (7.5 avg. EO) | 10.0 |
| Sodium $C_{12}$–$C_{14}$ alkyl sulfate | 7.0 |
| Water | Balance |

*Prepared as 90% R-2 reaction mixture in ethanol; entire mix is added to the detergent composition; fatty acids derived from $C_{12}$–$C_{16}$ coconut oil.

As can be seen from the latter two examples hereinabove, the present invention also encompasses a process for preparing a fully-formulated laundry detergent composition, or the like, comprising admixing the solvent-containing reaction product of the polyhydroxy fatty acid amide-forming R-2 reaction with otherwise conventional detersive surfactants and detersive adjuncts.

AQUEOUS SOLVENT EXAMPLES

Example IX

Adduct Formation

The following data are obtained by a standard process in which about 420 g of about 55% glucose solution (corn syrup—about 231 g glucose—about 1.28 moles) having a Gardner Color of less than 1 is reacted with about 119 g of about 50% aqueous methylamine (59.5 g of methylamine, —1.92 moles) solution. The methylamine (MMA) solution is purged and shielded with $N_2$ and cooled to about 10° C., or less. The corn syrup is purged and shielded with $N_2$ at a temperature of about 10°–20 ° C. The corn syrup is added slowly to the MMA solution at the indicated reaction temperature as shown. The Gardner Color is measured at the indicated approximate times in minutes.

TABLE 1

| Reaction Temp. °C. | Time in Minutes: | | | | | |
| --- | --- | --- | --- | --- | --- | --- |
| | 10 | 30 | 60 | 120 | 180 | 240 |
| | Gardner Color (Approximate) | | | | | |
| 0 | 1 | 1 | 1 | 1 | 1 | 1 |
| 20 | 1 | 1 | 1 | 1 | 1 | 1 |
| 30 | 1 | 1 | 2 | 2 | 4 | 5 |
| 50 | 4 | 6 | 10 | — | — | — |

As can be seen from the above data, the Gardner Color for the adduct is much worse as the temperature is raised above about 30° C. and at about 50° C., the time that the adduct has a Gardner Color below 7 is only about 30 minutes. For longer reaction, and/or holding times, the temperature should be less than about 20° C. The Gardner Color should be less than about 7, and preferably less than about 4 for good color glucamine.

When one uses lower temperatures for forming the adduct, the time to reach substantial equilibrium concentration of the adduct is shortened by the use of higher ratios of amine to sugar. With the 1.5:1 mole ratio of amine to sugar in this Example, equilibrium is reached in about two hours at a reaction temperature of about 30° C. At a 1.2:1 mole ratio, under the same conditions, the time is at least about three hours. For good color, the combination of amine:sugar ratio; reaction temperature; and reaction time is selected to achieve substantially equilibrium conversion, e.g., more than about 90%, preferably more than about 95%, even more preferably more than about 99%, based upon the sugar, and a color that is less than about 7, preferably less than about 4, more preferably less than about 1, for the adduct.

Using the above process at a reaction temperature of less than about 20° C. and corn syrups with different Gardner Colors as indicated, the MMA adduct color (after substantial equilibrium is reached in at least about two hours) is as indicated.

TABLE 2

| | Gardner Color (Approximate) | | | | | | |
| --- | --- | --- | --- | --- | --- | --- | --- |
| Corn Syrup | 1 | 1 | 1 | 1+ | 0 | 0 | 0+ |
| Adduct | 3 | 4/5 | 7/8 | 7/8 | 1 | 2 | 1 |

As can be seen from the above, the starting sugar material must be very near colorless in order to consistently have adduct that is acceptable. When the sugar has a Gardner Color of about 1, the adduct is sometimes acceptable and sometimes not acceptable. When the Gardner Color is above 1 the resulting adduct is unacceptable. The better the initial color of the sugar, the better is the color of the adduct.

Example X

Hydrogenation Reaction

Adduct from Example IX having a Gardner Color of 1 or less is hydrogenated according to the following procedure.

About 539 g of adduct in water and about 23.1 g of United Catalyst G49B Ni catalyst are added to a one liter autoclave and purged two times with 200 psig $H_2$ at about 20° C. The $H_2$ pressure is raised to about 1400 psi and the temperature is raised to about 50° C. The pressure is then raised to about 1600 psig and the temperature is held at about 50°–55° C. for about three hours. The product is about 95% hydrogenated at this point. The temperature is then raised to about 85° C. for about 30 minutes and the reaction mixture is decanted and the catalyst is filtered out. The product, after removal of water and MMA by evaporation, is about 95% glucamine, a white powder.

The above procedure is repeated with about 23.1 g of Raney Ni catalyst with the following changes. The catalyst is washed three times and the reactor, with the catalyst in the reactor, is purged twice with 200 psig $H_2$ and the reactor is pressurized with $H_2$ at 1600 psig for two hours, the pressure is released at one hour and the reactor is repressurized to 1600 psig. The adduct is then pumped into the reactor which is at 200 psig and 20° C., and the reactor is purged with 200 psig $H_2$, etc., as above.

The resulting glucamine in each case is greater than about 95% glucamine; has less than about 10 ppm Ni based upon the glucamine; and has a solution color of less than about Gardner 2.

The crude glucamine is stable to about 140° C.

It is important to have good adduct that has low sugar content (less than about 5%, preferably less than about 1%) and a good color (less than about 7, preferably less than about 4 Gardner, more preferably less than about 1).

Example XI

Adduct is prepared starting with about 159 g of about 50% methylamine in water, which is purged and shielded with $N_2$ at about 10°–20° C. About 330 g of about 70% corn syrup (near water white) is degassed with $N_2$ at about 50° C. and is added slowly to the methylamine solution at a temperature of less than about 20° C. The solution is mixed for about 30 minutes to give about 95% adduct that is a very light yellow solution.

About 190 g of adduct in water and about 9 g of United Catalyst G49B Ni catalyst are added to a 200 ml autoclave and purged three times with $H_2$ at about 20° C. The $H_2$ pressure is raised to about 200 psi and the temperature is raised to about 50° C. The pressure is raised to 250 psi and the temperature is held at about 50°–55° C. for about three hours. The product, which is about 95% hydrogenated at this point is then raised to a temperature of about 85° C. for about 30 minutes and the product, after removal of water and evaporation, is about 95% glucamine, a white powder.

The crude glucamine is stable to about 140° C.

It is also important to mimimize contact between adduct and catalyst when the $H_2$ pressure is less than about 1000 psig to mimimize Ni content in the glucamine. The nickel content in the glucamine in this reaction is about 100 ppm as compared to the less than 10 ppm in Example X.

Example XII

The following hydrogen reactions are run for direct comparison of reaction temperature effects.

A 200 ml autoclave reactor is used following typical procedures similar to those set forth in Examples X and XI to make adduct and run the hydrogen reaction at various temperatures.

Adduct for use in making glucamine is prepared by combining about 420 g of about 55% glucose (corn syrup) solution (231 g glucose; 1.28 moles) (The solution is made using 99DE corn syrup from CarGill, the solution having a color less than Gardner 1) and about 119 g of 50% methylamine (59.5 g MMA; 1.92 moles) (from Air Products ).

The reaction procedure is as follows:
1. Add about 119 g of the 50% methylamine solution to a $N_2$ purged reactor, shield with $N_2$ and cool down to less than about 10° C.
2. Degas and/or purge the 55% corn syrup solution at 10°–20° C. with $N_2$ to remove oxygen in the solution.
3. Slowly add the corn syrup solution to the methylamine solution and keep the temperature less than about 20° C.
4. Once all corn syrup solution is added in, agitate for about 1–2 hours.

The adduct is used for the hydrogen reaction right after making, or is stored at low temperature to prevent further degradation.

The glucamine adduct hydrogen reactions are as follows:
Conditions with Temperature Change at the End:
1. Add about 134 g adduct (color less than about Gardner 1) and about 5.8 g G49B Ni to a 200 ml autoclave.
2. Purge the reaction mix with about 200 psi $H_2$ twice at about 20°–30° C.
3. Pressure with $H_2$ to about 400 psi and raise the temperature to about 50° C.
4. Raise pressure to about 500 psi, react for about 3 hours. Keep temperature at about 50°–55° C. Take sample 1.
5. Raise temperature to about 85° C. for about 30 minutes.
6. Decant and filter out the Ni catalyst. Take sample 2.

Conditions for Constant Temperature Reactions:
1. Add about 134 g adduct and about 5.8 g G49B Ni to a 200 ml autoclave.
2. Purge with about 200 psi $H_2$ twice at low temperature.
3. Pressure with $H_2$ to about 400 psi and raise temperature to about 50° C.
4. Raise pressure to about 500 psi, react for about 3.5 hours. Keep temperature at indicated temperature.
5. Decant and filter out the Ni catalyst. Sample 3 is for about 50°–55° C.; Sample 4 is for about 75° C.; and Sample 5 is for about 85° C. (The reaction time for about 85° C. is about 45 minutes.)

As used herein "psi" means "psig" unless otherwise stated.

| Samples and Analysis | | | | | |
|---|---|---|---|---|---|
| | Sample: | | | | |
| | 1 | 2 | 3 | 4 | 5 |
| Analysis | | | | | |
| Color (Gardner) | 0+ | 4– | 3 | 4 | 7 |
| Color (Gardner) Stability (140° C. for 10 Min.) | 14 | 6 | 13 | 15 | 16 |
| Analysis by Gas Chromatograph | | | | | |
| N-Methylglucamine | 93.5% | 93.4% | 94.0% | 94.5% | 95.5% |
| Sorbitol | 0.78% | 0.67% | 0.54% | 0.80% | 1.0% |
| Unreacted Adduct | 0.4% | 0.16% | 0.54% | 0.36% | 0.34% |
| Glucose | — | — | — | — | — |
| DiGlucosamine | 0.87% | — | 1.31% | 0.72% | 0.57% |
| Ni (ppm) | — | 28 | 24 | 24 | 21 |
| Temperature °C. | 55 | 55/85 | 55 | 75 | 85 |

As can be seen from this data, all runs give similar purity of N-methylglucamine (about 94%); the Gardner Colors of the runs are similar right after reaction, but only the two-stage heat treatment gives good color stability; and the 85° C. run gives marginal color immediately after reaction.

Example XIII

Catalyst Treatment

Approximately 300 mls of RANEY NICKEL 4200 (Grace Chemicals) is washed with deionized water (1 liter total volume; 3 washings) and decanted. The total catalyst solids can be determined by the volume-weight equation provided by Grace Chemicals, i.e., [(total wt. catalyst+water)–(water wt. for volume)]×7/6=Nickel solids.

308.21 g. of the catalyst Ni solids basis are loaded into a 2 gallon reactor (316 stainless steel baffled autoclave with DISPERSIMAX hollow shaft multi-blade impeller from Autoclave Engineers) with 4 liters of water. The reactor is heated to 130° C. at 1400–1600 psig hydrogen for 50 minutes. The mixture is cooled to room temperature at 1500 psig hydrogen and left overnight. The water is then removed to 10% of the reactor volume using an internal dip tube.

Reaction

The reactants are as follows. 881.82 mls. 50% aqueous monomethylamine (Air Products, Inc.; Lot 060-889-09); 2727.3 g. 55% glucose syrup (Cargill; 71% glucose; 99 dextrose equivalents; Lot 99M501).

The reactor containing the $H_{2O}$ and Raney nickel prepared as noted above is cooled to room temperature and ice cold monomethylamine is loaded into the reactor at ambient pressure with $H_2$ blanket. The reactor is pressurized to 1000 psig hydrogen and heated to 50° C. for several minutes. Stirring is maintained to assure absorption of $H_2$ in solution.

The glucose is maintained in a separate reservoir which is in closed communication with the reactor. The reservoir is pressurized to 4000 psig with hydrogen. The glucose (aqueous solution) is then transferred into the reactor under $H_2$ pressure over time. (This transfer can be monitored by the pressure change in the reservoir resulting from the decrease in volume of the sugar solution as it is transferred from the reservoir into the main reactor. The sugar can be transferred at various rates, but a transfer rate of ca. 100 psig pressure drop per minute is convenient and requires about 20 minutes for the volume used in this run.) An exotherm occurs when the aqueous sugar solution is introduced into the reactor; the 50° C. internal temperature raises to ca. 53° C.

Once all the glucose has been transferred to the reactor the temperature is maintained at 50° C. for 30 minutes. Hydrogen uptake is monitored by a pressure gauge. Stirring is continued throughout at 800–1,100 rpm or greater.

The temperature of the reactor is increased to 60° C. for 40 minutes, then to 85° C. for 10 minutes, then to 100° C. for 10 minutes. The reactor is then cooled to room temperature and maintained under pressure overnight. The reaction product dissolved in the aqueous reaction medium is conveniently recovered by using an internal dip tube with hydrogen pressure. Particulate nickel can be removed by filtration. Preferably, an internal filter is used to avoid exposure to air, which can cause nickel dissolution. Solid N-methyl glucamine is recovered from the reaction product by evaporation of water.

The procedure of Example I is repeated using fructose as the sugar to prepare N-methyl fructamines.

The procedure of Example I is repeated using glyceraldehyde as the sugar to prepare N-methyl glycerol amine (3-methylamino-1,2-propanediol).

Example XIV

In this process, the N-methyl glucamine of Example I is reacted with mixed tallow fatty acid methyl esters to prepare the corresponding tallowamide of N-methyl glucamine. It will be appreciated that coconut fatty acid methyl esters can be used in place of the tallow reactant, and various N-alkyl polyols, e.g., N-methyl fructamine, can be used in place of the N-methyl glucamine.

Reactants

N-methyl glucamine (from Example I); hardened tallow methyl esters; sodium methoxide (25% in methanol); absolute methanol (solvent); mole ratio approximately 1:1 amine:ester; initial catalyst level 10 mole % (w/r glucamine), raised to 20 mole %; solvent level 50% (wt.).

In a sealed bottle, 20.36 g of the tallow methyl ester is heated to its melting point (water bath) and loaded into a 250 ml 3-neck round-bottom flask with mechanical stirring. The flask is heated to ca. 70° C. to prevent the ester from solidifying. Separately, 12.5 g of dry N-methyl glucamine is combined with 45.36 g of methanol, and the resulting slurry is added to the tallow ester with good mixing. 1.51 g of 25% sodium methoxide in methanol is added. If after about four hours the reaction mixture is not clarified, an additional 10 mole % of catalyst (to a total of 20 mole %) can be added and the reaction allowed to continue overnight (ca. 68° C.) after which time the mixture is clear. The reaction flask is then modified for distillation. The bath temperature is increased to 110° C. Distillation at atmospheric pressure is continued for 60 minutes. High vacuum distillation is then begun. The product is allowed to remain in the reaction flask at 110° C. (external temperature) for 60 minutes. The product is scraped from the flask and optionally triturated in ethyl ether over a weekend. Ether is removed on a rotary evaporator and the product is stored in an oven overnight, and ground to a powder. The reaction product can optionally be purified for analysis, as follows. Any remaining N-methyl glucamine is optionally removed from the product using silica gel. A silica gel slurry in 100% methanol is loaded into a funnel and washed several times with 100% methanol. A concentrated sample of the product (20 g in 100 ml of 100% methanol) is loaded onto the silica gel and eluted several times using vacuum and several methanol washes. The collected eluant is evaporated to dryness (rotary evaporator). Any remaining tallow ester is optionally removed by trituration in ethyl acetate overnight, followed by filtration. The filter cake is then vacuum dried overnight. The product is the purified tallowalkyl N-methyl glucamide. NOTE: Such a high level of purification is unnecessary for routine use of the tallowalkyl N-methyl glucamide in detergent compositions, since the product will typically have an acceptable Gardner Color by virtue of the quality of the N-alkyl glucamine prepared by the instant process. Accordingly, this purification step will be at the discretion of the formulator.

In another mode, the foregoing reaction sequence can be carried out in 1,2-propylene glycol or NEODOL. At the discretion of the formulator, the propylene glycol or NEODOL need not be removed from the reaction product prior to its use to formulate detergent compositions. Again, according to the desires of the formulator, the nethoxide catalyst can be neutralized by citric acid to provide sodium citrate, which can remain in the polyhydroxy fatty acid amide.

What is claimed is:

1. A process, carried out under non-oxidizing conditions, for preparing N-alkylamino polyols, said process being selected from the group consisting of:

(A) a process using a preformed adduct, comprising the steps of:

(a) preparing an adduct of a reducing sugar and a primary amine, comprising reacting a solution of said sugar, having a Gardner Color of less than about 1 and being essentially free of oxygen, with said amine, which is also essentially free of oxygen, at a temperature that is less than about 70° C., the molar ratio of said amine to said sugar being less than about 30:1, and the time of the reaction being short enough to give a Gardner Color of less than about 7 and long enough to give yield of adduct based on said sugar of at least about 90%;

(b) reacting said adduct from Step (a), said adduct being substantially free from unreacted sugar starting material and said adduct being dissolved/ suspended in aqueous solvent, with hydrogen in the presence of a hydrogenation catalyst, in two stages, the first stage being at a temperature of from about 20° C. to about 70° C. and a hydrogen pressure of more than about 100 psi to convert at least about 80% of said adduct to the corresponding amine and the second stage being at a temperature of more than about 75° C. to convert any remaining adduct and destroy any color material precursors; and (c) removing said catalyst; and (B) a process in which a reducing sugar is added to a mixture of a nickel catalyst and N-alkylamine containing substantially no oxides of nickel comprising the steps of:

(a) admixing the nickel catalyst with the N-alkylamine to provide mixture (a) under $H_2$ pressure prior to admixture with the sugar;

(b) admixing the sugar with mixture (a) under hydrogen pressure;

(c) conducting the reaction of the sugar with the N-alkylamine/nickel catalyst mixture (a) at a temperature below about 80° C. and under hydrogen pressure until at least about 95% of reducible compounds are no longer present in the reaction mixture;

(d) continuing the reaction of step (c), optionally at a temperature of up to about 120° C., until at least about 99.9% of the reducible compounds are no longer present in the reaction mixture; and (e) recovering the N-alkylamino polyol;

the catalyst in process (A) optionally being nickel, any said nickel catalyst in process (A) or process (B) being maintained under conditions of temperature and hydrogen pressure when in contact with either said adduct; said N-alkylamino polyol; or mixtures thereof to minimize solubilization of said nickel, and any said nickel catalyst optionally being washed with solvent and treated with hydrogen to substantially remove all, when present, of oxides of nickel; organic materials; excess caustic; alumina fines; or mixtures thereof; and, also, optionally, after said processes are substantially complete, providing an improvement selected from the group consisting of: maintaining the temperature at about 20° C. to about 135° C., and the hydrogen pressure higher than 100 psig to deposit solubilized nickel and regenerate said nickel catalyst; separating said nickel catalyst from said N-alkylamino polyol at low temperature under non-oxidizing atmosphere; and combinations thereof.

2. A process according to claim 1, process (B), comprising an improvement selected from the group consisting of: said nickel catalyst being washed with solvent and treated with hydrogen to substantially remove all, when present, of oxides of nickel; organic materials; excess caustic; alumina fines; and mixtures therof; after said processes are substantially complete, providing an improvement selected from the group consisting of: maintaining the temperature at about 20° C. to about 135° C. and the hydrogen pressure higher than 100 psig to deposit solubilized nickel and regenerate said nickel catalyst; separating said nickel catalyst from said N-alkylamino polyol at low temperature under non-oxidizing atmosphere; and combinations thereof.

3. A process according to claim 2 wherein the nickel catalyst level is in the range of from about 5% to about 30%, by weight of sugar reactant.

4. A process according to claim 2 wherein the oxides of nickel are removed by contacting the nickel catalyst with hydrogen.

5. A process according to claim 2 wherein step (d) is carried out at a temperature of from about 40° C. to about 70° C.

6. A process according to claim 2 wherein step (e) is carried out at a temperature of from about 80° C. to about 120° C.

7. A process according to claim 2 for the preparation of N-alkyl glucamine, N-alkyl fructamine, N-alkyl maltamine or N-alkyl glycerol amine, respectively, comprising the steps of:

(a) admixing a nickel catalyst which is substantially free of oxides of nickel with an N-alkylamine;

(b) under hydrogen pressure, admixing an aqueous sugar solution of glucose, fructose, maltose, xylose or glyceraldehyde, respectively, with the mixture from step (a);

(c) allowing the mixture from step (b) to react at a temperature from about 40° C. to about 70° C. until at least about 95% of the reducible compounds are no longer present in the reaction mixture; and (d) allowing the reaction from step (c) to continue at a temperature below about 120° C. until at least about 99.9% of the reducible compounds are no longer present in the reaction mixture.

8. A process according to claim 7 wherein the nickel catalyst is pre-treated with hydrogen to remove oxides of nickel, and is present at the 5% to 30% level based on sugar.

9. A process according to claim 7 wherein the N-alkylamine is N-methylamine.

10. A process according to claim 1, process (A), carried out under non-oxidizing conditions, for preparing N-alkyl polyhydroxy amines, comprising the steps of:

a) reacting said adduct from said process (A), step (a), said adduct being substantially free from unreacted sugar starting material and said adduct being dissolved/suspended in aqueous solvent, with hydrogen in the presence of a hydrogenation catalyst, in two stages, the first stage being at a temperature of from about 20° C. to about 70° C. and a hydrogen pressure of more than about 100 psi to convert at least about 80% of said adduct to the corresponding amine and the second stage being at a temperature of more than about 75° C. to convert any remaining adduct and destroy any color material precursors; and b) removing said catalyst.

11. A process according to claim 10 wherein said first stage of Step (a) is carried out at a temperature of from about 40° C. to about 65° C. and said second stage is carried out at a temperature of from about 80° C. to about 135° C.

12. A process according to claim 11 wherein the amine compound is a member selected from the group consisting of $C_1$-$C_4$ alkyl or hydroxyalkyl amines.

13. A process according to claim 12 wherein the sugar is glucose.

14. A process according to claim 13 wherein the amine is monomethyl amine, whereby N-methylglucamine is secured.

15. A process according to claim 10 wherein the catalyst in Step (a) is a particulate nickel catalyst.

16. A process according to claim 15 wherein the catalyst is particulate catalyst comprising nickel on a substrate material.

17. A process according to claim 15 wherein the amount of time the adduct and the catalyst are present together before the $H_2$ pressure is raised to at least about 500 psig is less than about one hour.

18. A process according to claim 17 wherein said amount of time is less than about one-half hour.

19. A process, carried out under non-oxidizing conditions, for preparing N-alkyl polyhydroxy amines, comprising the steps of:

a) reacting an adduct of a reducing sugar and a primary amine, said adduct being dissolved/suspended in aqueous and/organic hydroxy solvent, with hydrogen in the presence of a catalyst, in two stages, the first stage being at a temperature that is sufficiently low to avoid said adduct's degradation and/or excessive formation of the hydrogenated material corresponding to the said reducing sugar and minimizing the time that said adduct and said catalyst are admixed before the hydrogen pressure is sufficiently high to avoid creating color precursors and oxidized catalyst from said adduct, to convert at least about 80% of said adduct to the corresponding amine of said reducing sugar and the second stage being at a temperature sufficiently high to minimize any remaining adduct and any color material precursors; and b) removing said catalyst.

20. A process according to claim 19 wherein said first stage of Step (a) is carried out at a temperature of less than about 70° C. and said second stage is carried out at a temperature of less than about 135° C.

21. A process according to claim 20 wherein the amine compound is a member selected from the group consisting of $C_1$–$C_4$ alkyl or hydroxyalkyl amines.

22. A process according to claim 21 wherein the sugar is glucose.

23. A process according to claim 22 wherein the amine is monomethyl amine, whereby N-methylglucamine is secured.

24. A process according to claim 19 wherein the catalyst in Step (a) is a particulate nickel catalyst.

25. A process according to claim 24 wherein the catalyst is a particulate catalyst comprising nickel on a substrate material.

26. A process for preparing an adduct of a primary amine and a reducing sugar in aqueous solvent wherein said sugar has a Gardner Color of less than about 1, and wherein said process is carried out under a combination of temperature, time and ratio of amine to said sugar to give an equilibrium product having an adduct level that is at least 90%, based upon said sugar and a Gardner Color of less than about 7.

27. The process of claim 26 wherein said sugar has a Gardner Color of less than about 0+ and said equilibrium product has an adduct level of at least about 95% and a Gardner Color of less than about 4.

28. A process, carried out under non-oxidizing conditions, for preparing an adduct of a reducing sugar and a primary amine, comprising reacting a solution of said sugar, having a Gardner Color of less than about 1 and being essentially free of oxygen, with said amine, which is also essentially free of oxygen, at a temperature that is less than about 70° C., the molar ratio of said amine to said sugar being less than about 30:1, and the time of the reaction being short enough to give a Gardner Color of less than about 7 and long enough to give yield of adduct based on said sugar of at least about 90%.

29. The process of claim 28 wherein said sugar solution is aqueous and said molar ratio of said amine to said sugar is less than about 7:1.

30. The process of claim 29 wherein said temperature is less than about 30° C. and the molar ratio of amine to sugar is less than about 2:1.

31. The process of claim 29 wherein said aqueous solution of sugar has a Gardner Color of less than about 0+.

32. The process of claim 30 wherein said aqueous sugar solution is corn syrup and said amine is monoalkyl or monohydroxyalkyl amine containing from one to about 4 carbon atoms.

33. The process of claim 28 which is a batch process and wherein said temperature is less than about 30° C.

34. The process of claim 28 wherein said temperature is above about 30° C. and said time is less than about one-half hour.

35. The process of claim 34 wherein said temperature is above about 50° C. and said time is less than about ten minutes.

36. The process of claim 35 which is a continuous process with essentially plug flow characteristics.

37. A process, carried out under non-oxidizing conditions, for preparing N-alkyl polyhydroxy amines, comprising the steps of:

(a) reacting the adduct prepared by the process of claim 28, said adduct being dissolved/suspended in aqueous and/or organic hydroxy solvent, with hydrogen in the presence of a catalyst, in two stages, the first stage being at a temperature that is sufficiently low to avoid said adduct's degradation and/or excessive formation of the hydrogenated material corresponding to the said reducing sugar and minimizing the time that said adduct and said catalyst are admixed before the hydrogen pressure is sufficiently high to avoid creating color precursors from said adduct and/or oxidizing said catalyst, to convert at least about 80% of said adduct to the corresponding amine of said reducing sugar and the second stage being at a temperature sufficiently high to minimize any remaining adduct and any color material precursors; and b) removing said catalyst.

* * * * *